(12) United States Patent
Spector et al.

(10) Patent No.: US 9,913,748 B2
(45) Date of Patent: Mar. 13, 2018

(54) METHOD AND APPARATUS FOR TREATMENT OF ERECTILE DYSFUNCTION WITH EXTRACORPOREAL SHOCKWAVES

(76) Inventors: Avner Spector, Savyon (IL); Michal Jeshurun-Gutshtat, Elkana (IL); Gil Hakim, Raanana (IL)

( * ) Notice: Subject to any disclaimer, the term of this patent is extended or adjusted under 35 U.S.C. 154(b) by 1219 days.

(21) Appl. No.: 13/504,499

(22) PCT Filed: Oct. 3, 2010

(86) PCT No.: PCT/IL2010/000804
§ 371 (c)(1),
(2), (4) Date: Apr. 27, 2012

(87) PCT Pub. No.: WO2011/051928
PCT Pub. Date: May 5, 2011

(65) Prior Publication Data
US 2012/0215142 A1    Aug. 23, 2012

Related U.S. Application Data

(60) Provisional application No. 61/256,373, filed on Oct. 30, 2009.

(51) Int. Cl.
| *A61H 23/00* | (2006.01) |
| *A61F 5/41* | (2006.01) |
| *A61B 17/225* | (2006.01) |

(52) U.S. Cl.
CPC ............ *A61F 5/41* (2013.01); *A61B 17/2251* (2013.01); *A61H 23/008* (2013.01); *A61F 2005/417* (2013.01); *A61H 2201/0153* (2013.01); *A61H 2205/086* (2013.01); *A61H 2205/087* (2013.01)

(58) Field of Classification Search
CPC ........ A61H 19/00; A61H 23/00; A61H 23/02; A61H 23/008; A61H 23/0245; A61H 2205/085; A61H 2205/086; A61H 2205/087; A61F 5/41; A61F 2005/411; A61F 2005/412; A61F 2005/417
USPC .......................................................... 600/38
See application file for complete search history.

(56) References Cited

U.S. PATENT DOCUMENTS

| 5,125,890 | A | * | 6/1992 | Merrill | ...................... | A61F 5/41 |
| | | | | | | 600/39 |
| 5,669,869 | A | * | 9/1997 | Strom | ........................ | A61F 5/41 |
| | | | | | | 600/38 |
| 2002/0055702 | A1 | * | 5/2002 | Atala | ................. | A61M 37/0092 |
| | | | | | | 604/20 |
| 2006/0100552 | A1 | * | 5/2006 | Schultheiss | .......... | A61H 23/008 |
| | | | | | | 601/2 |
| 2006/0106327 | A1 | * | 5/2006 | Thielen | .................. | A61H 19/34 |
| | | | | | | 601/46 |

FOREIGN PATENT DOCUMENTS

WO    WO 2005/099366    * 10/2005    ............. A61H 19/30

* cited by examiner

*Primary Examiner* — Quang D Thanh
(74) *Attorney, Agent, or Firm* — Shalom Wertsberger; Saltamar Innovations

(57) ABSTRACT

A method and device producing extracorporeal shockwaves for the treatment of erectile dysfunction.

26 Claims, 6 Drawing Sheets

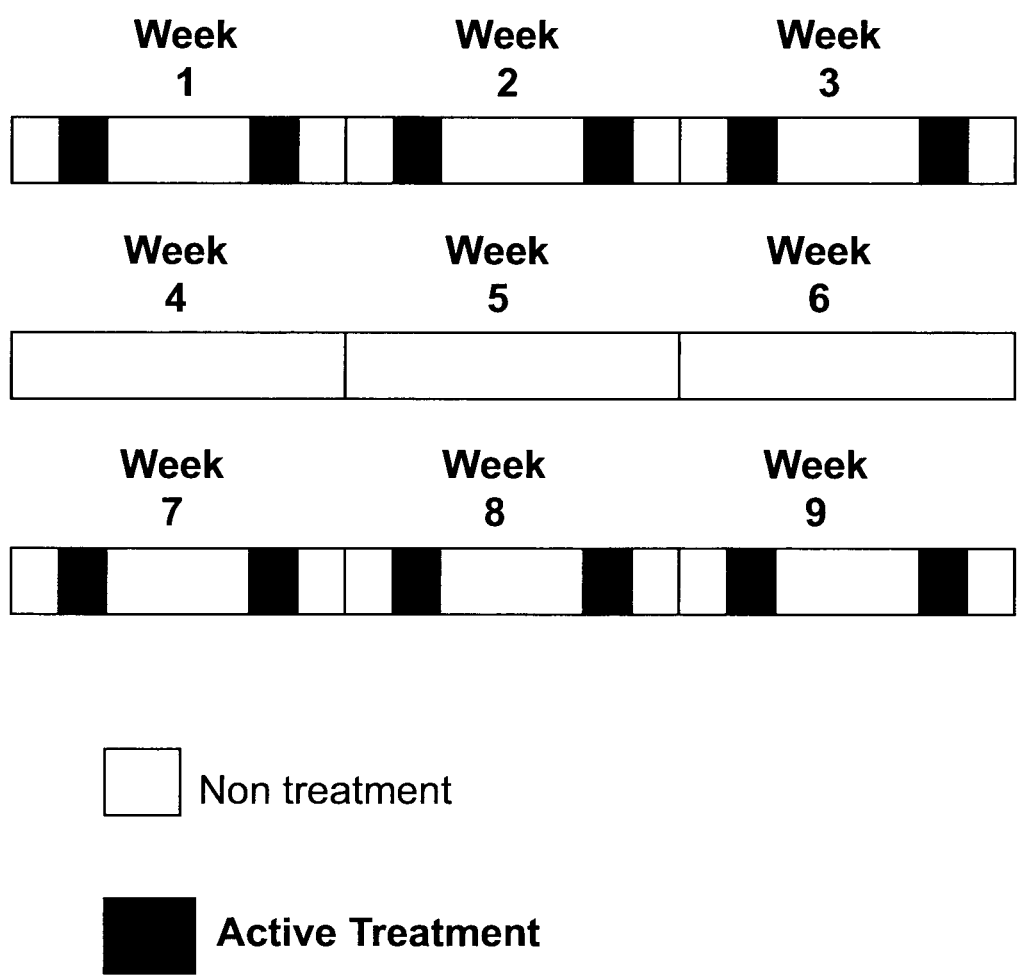

METHOD AND APPARATUS FOR TREATMENT OF ERECTILE DYSFUNCTION WITH EXTRACORPOREAL SHOCKWAVES

CROSS-REFERENCE TO RELATED APPLICATIONS

This application is the U.S. national phase application of PCT International Application No. PCT/IL2010/000804, filed on 3 Oct. 2010, which claims the benefit of U.S. Provisional Application Ser. No. 61/256,373, filed on 30 Oct. 2009, all of which are hereby incorporated by reference in their entirety.

FIELD OF THE INVENTION

The present invention relates to a method and device producing extracorporeal shockwaves and in particular, to such a method and device for the treatment of erectile dysfunction.

BACKGROUND OF THE INVENTION

Extracorporeal shock wave therapy (ESWT) is non-surgical, noninvasive treatment of medical conditions using acoustic shock waves. First use of shockwave therapy in the early 1980's was utilized to fragment kidney stones termed shockwave lithotripsy. Continued development of shockwave treatment showed the possibility of stimulating bone formation, angiogenesis, as well as other orthopedic indications.

A shock wave is a type of acoustic energy resulting from phenomena, such as an explosion or lightning, that create a sudden intense change in pressure. The intense changes in pressure produce strong waves of energy that can travel through any elastic medium such as air, water, human soft tissue, or certain solid substances such as bone.

Acoustic shock waves for ESWT are primarily generated by three different methods, electrohydraulic (also referred to as spark gap), electromagnetic (also referred to as EMSE), and piezoelectric. Each method needs and apparatus to focus the generated shockwave so as to provide a focal point and/or focal zone for the treatment area. In the focal zone, the shock waves produce much higher pressure impulses as compared with the zone outside of the focal zone. Mechanical focusing for each of these methods is generally realized with an appropriate arrangement of surfaces reflecting the wave toward the desired focal point and/or an appropriate arrangement of the generating devices.

Spark gap systems incorporate an electrode (spark plug) to initiate a shock wave and ellipsoid to focus it. EMSE systems utilize an electromagnetic coil and an opposing metal membrane. Piezoelectric systems form acoustical waves by mounting piezoelectric crystals to a spherical surface to provide focus. Of the three systems, the spark gap system is generally preferred in the art for ESWT as it utilizes more of the generated shockwave energy to the treatment target site.

In spark gap systems, high energy shock waves are generated when electricity is applied to an electrode positioned in an ellipsoid immersed in treated water. When the electrical charge is fired, a small amount of water is vaporized at the tip of the electrode and a shock wave is produced. The shock wave ricochets from the side of an ellipsoid and converges at a focal point, which may then be transferred to the area to be treated.

In electromagnetic systems an electrical impulse is circulated in a coil. The coil produces an electromagnetic field that expels a metallic membrane to produce the mechanical impulse.

In piezoelectric systems a ceramic material with piezoelectric characteristics is subjected to an electrical impulse. The electric impulse modifies the dimension of the ceramic material to generate the desired mechanical impulse. A focal point is attained by covering a concave spherical surface with piezoelectric ceramics converging at the center of the sphere.

The method of focusing the generated shockwave has been greatly described in the art for example in U.S. Pat. Nos. 5,174,280 and 5,058,569, U.S. Pat. No. 5,033,456, EP1591070 all of which are incorporated herein by reference as if fully set forth.

Medical use of shockwave therapy provides noninvasive means for treating a variety of anomalies such as kidney stones, chronic orthopedic inflammation healing, bone healing, wound healing, osteogenesis, revascularization, angiogenesis are known in the art. ESWT has also been described in attempts to treatment of Peyronie's disease.

Peyronie's disease consisting of penile deformity and angulation has been treated with shockwave therapy since early 80's. Such shockwave treatment attempts to soften plaques formed in the tunica abluginea causing painful erection and penile deformation, as well as improving its elastic nature. Recently reported Peyronie's treatment regimen includes five (5) sessions where each session provides 3000 shockwave with emission frequency of 120 waves/min, energy intensity of 0.11 to 0.17 mJ/mm$^2$, International Journal of Impotence Research (2004) 16, 448-451; similar treatment regiments were also reported in J Endourol. 2005 January-February, vol. 19(1):11-4. The ESWT for Peyronie's is primarily set to soften the plaque causing penile deformation and angulation, as well as increasing the vascularity of the area of the plaque.

Erectile dysfunction (referred to herein as ED) can be caused by physiologic, neurogenic, vasculogenic, hormonal, or psychological factors. The term "erectile dysfunction", as used herein, refers to the inability or impaired ability of a male individual to experience a penile erection.

Normal erectile function requires adequate penile arterial inflow, sufficient corpora cavernosal expansion, and competent venous sinusoidal outflow occlusion. Severe malfunction of any one of these components, or a cumulative failure of multiple components, will result in erectile failure leading to erectile dysfunction. Improved treatment of erectile dysfunction has made it necessary to access erectile physiology more accurately in order to determine which vascular component is dysfunctional and to distinguish whether a patient suffers from a physiologic, neurogenic, vasculogenic, hormonal, or psychologic etiology for his erectile dysfunction.

The penis is divided into four hydraulic chambers: two corpora cavernosa, a corpus spongiosum, and a glans. Although all contain sponge-like sinusoidal tissue, only the corpora cavernosal sinusoids contain the venous sinusoidal occlusion mechanism. By permitting blood to flow into but not out of the corpus cavernosum, the venous sinusoidal mechanism can transform the corpus cavernosum from an open to a closed chamber capable of trapping blood and thus producing rigid erections.

Under normal circumstances, each corpus cavernosum is supplied by its own cavernosal artery. Cavernosal artery flow and pressure determine the competence of the erectile process. The dorsal and bulbar arteries supply blood to the skin of the penis, glans, and corpus spongiosum, playing only a minor role in the erectile process.

The erectile cycle can be divided into four phases: initiation, generation, maintenance, and detumescence. The earliest phase of erection, initiation, occurs when a neurochemical stimulus causes a rapid inflow of arterial blood into the corpora. The sinusoids become engorged. Generation occurs when the venous outflow mechanism closes. Blood is then stored in the corpora cavernosal bodies. The penis expands until full rigidity is achieved. Maintenance occurs when the corporal bodies are fully expanded and the arterial inflow and venous outflow are in an equilibrium state such that full penile expansion and pressure are maintained. Detumescence is the process whereby full erection is lost by either a decrease in arterial inflow or an increase in venous sinusoidal outflow.

Urologists and practitioners have devised a number of therapies for treating erectile dysfunction. These therapies include psychological, surgical, pharmacological, ultrasound and electrical therapies.

Method and devices for electrically stimulating a penile erection are disclosed in U.S. Pat. No. 4,585,005 to Lue et al; U.S. Pat. No. 5,571,118 to Boutos and U.S. Pat. No. 4,542,753 respectively.

Pharmacological therapies for erectile dysfunction include the injection of drugs into the penis, urethra as disclosed in U.S. Pat. No. 5,236,904 to Gerstengerg et al. and U.S. Pat. No. 4,127,118 to Latorre. More recently oral drugs, such as VIAGRA®, have been used to treat ad hoc episodes of ED have been widely used for the maintenance of an erection.

U.S. Pat. No. 6,469,012 to Ellis et al assigned to Pfizer teaches an orally administered drug comprising pyrazolopyrimidinones sold under the brand name VIAGRA® teaches the selective enzymatic inhibition of potent inhibitors of cyclic guanosine 3',5'-monophosphate phosphodiesterases (cGMP PDEs) in contrast to their inhibition of cyclic adenosine 3',5'-monophosphate phosphodiesterases (cAMP PDEs) that leads to elevated cGMP levels in the corpus cavernosum that then brings about the relaxation of the corpus cavernosum tissue and consequently mediating penile erection PCT Publication WO9912514 to Redano teaches an apparatus and method for treating erectile dysfunction using ultrasound penile treatment by stimulating hemodynamic activity within a penis by increasing hemodynamic flow to the penis with the use of ultrasound energy source to the outer surface of a penis. Redano also teaches an ultrasonograph measuring one or more hemodynamic parameters within the penis, for example blood flow velocity, blood pressure, and/or blood temperature that may be used to determine treatment or cause for erectile dysfunction.

A further treatment for Erectile Dysfunction known in the art comprises a vacuum pump or a Vacuum Constricting Devices (VCD) comprising a housing for the penis coupled to a pump and a constricting ring. The housing is placed over the penis and coupled to an air pump to create a vacuum within the housing over the penis therein urging blood into the penis to mediate an erection while a constricting ring is placed over the base of the penis to constrict blood flow out of the penis to maintain the erection. While the various VCD solutions do bring about an erection they do not treat the underlying causes of Erectile Dysfunction therefore providing an ad hoc solution to ED.

Other treatments of ED know in the art includes invasive and/or long treatments such as intraurethral suppositories, vascular surgery in case of arterial insufficiency, penile implants, hormone therapy and psychosexual treatment.

SUMMARY OF THE INVENTION

There is an unmet need for, and it would be highly useful to have, a device and a method providing extracorporeal shock wave therapy (ESWT) for erectile dysfunction that provides for treatment of chronic ED rather than the ad hoc solutions offered by the prior art treatments for example pharmacological (VIAGRA®) or physiological (VCD) solutions.

Within the context of this application the terms aqueous solution, aqueous medium, or aqueous environment may be used interchangeably to refer to an enclosure, opening, lumen, or space that is placed in an aqueous solution or mixture for example including but not limited to water, medicated water, ionized water, oil, gel, treated water or the like solution or mixture in a liquid state.

Within the context of this application the term extracorporeal shock wave therapy (ESWT) refers to shock wave therapy provided with a shock wave generating device.

Within the context of this application the term shockwave treatment device refers to a device comprising a controller and/or computer and a shockwave treatment applicator as is known in the art. For example, a shockwave treatment device comprises controller and/or computer that controls the shockwave treatment produced by the shockwave treatment applicator.

An optional embodiment of the present invention provides for a method for the treatment of Erectile Dysfunction, the method comprising: associating a penis with a shockwave generating device within an aqueous environment; and applying a shockwave regimen to the penis. Preferably the shockwave device produces a focal treatment zone comprising at least a portion of the treated penis. More preferably the shockwave device produces a focal treatment zone comprising from about 50% to about 100% of the treated penis.

Optionally the focal treatment zone according to the present invention comprises least one of about 7 treatment zones along the penis, FIG. 5A-B. Optionally a plurality of the 7 treatment zones may be treated simultaneously, FIG. 5A-B. Most preferably a single focal treatment zone including most of the penis may be provided by the shockwave treatment apparatus according to the present invention, FIG. 5B. Optionally the focal treatment zone includes most of the corpus cavernosa along the length of the penis.

Optionally the single focal treatment zone is provided with a length comprising the length of the penis. Optionally the single focal treatment zone is provided with a width comprising the width of the penis. Most preferably the single focal treatment zone is provided with a length and width comprising the length and width of the penis.

Optionally, the method of treatment of ED according to the present invention of promotes at least one or more therapies for treating symptoms of Erectile Dysfunction for example including but not limited to vasodilatation, vasoconstriction, endothelial function, angiogenesis, neuronal, neural regeneration, decalcification, increase cytoplasmic calcium concentration, reduce cytoplasmic calcium concentration, inhibition of PDE5, enzymatic inhibition, enzymatic excitation, any combination thereof, or the like.

Optionally, the method of treatment of ED according to the present invention produces a shock wave regimen determined based on at least one or more parameters for example including but not limited to shockwave parameters, treatment protocol parameters, anatomical parameters, or the like.

Optionally protocol parameters for example including but not limited to the number of treatments sessions, the duration of a treatment protocol, timing of active and/or inactive treatment sessions, frequency of session, or the like.

Optionally the number of active treatment sessions may be provided from about 3 sessions to about 18 sessions. Optionally 12 active treatments may be provided during the treatment protocol according to the present invention.

Optionally the duration of the treatment protocol according to the present invention may be from about 3 weeks to about 18 weeks.

Optionally, shockwave parameters may for example include but are not limited to number of shockwaves, frequency of shockwaves and intensity of the shockwave, or the like.

Optionally shockwave intensity may be provided from about 0.02 mJ/mm$^2$ to about 0.18 mJ/mm$^2$. Optionally and preferably a shockwave intensity may be provided at about 0.09 mJ/mm$^2$.

Optionally shockwave frequency may be provided from about 60 shockwaves per minute to about 240 shockwaves per minute. Optionally and preferably a shockwave frequency may be provided at about 120 shockwaves per minute.

Optionally the number of shockwaves per treatment session may be provided from about 300 shockwave up to about 5000 shockwaves. Optionally and preferably about 3500 shockwaves per session may be provided.

Optionally and preferably the anatomical parameters may for example include but are not limited to at least one of 8 zones along of the penis, preferably from the glans to the penis root, for example zones 1-7 as shown in FIG. 5A. Optionally the anatomical parameters comprise at least one focal zone including most of the corpus cavernosa of the penis. More preferably the anatomical parameters comprise a single focal zone including most of the corpus cavernosa of the penis, as shown in FIG. 5B.

Optionally the method for treatment of ED according to the present invention may be provided within vacuum environment from about 0.1 atm to about 0.8 atm. Optionally the vacuum environment is provided within an aqueous environment. Optionally the liquid environment may provided by a liquid or solution for example including but not limited to water, medicated water, ionized water, oil, gel, treated water or the like solution or mixture in a liquid state.

Optionally the method of treatment of ED according to the present invention may be provided with a drug and/or medicinal treatment. Optionally the drug and/or medicament may for example include but is not limited to stem cells, growth factors, hormones, peptides, biologics, DNA, RNA, animal extract, plant extract, oil, gel, balm, cream, angiogenic drugs, or the like.

Optionally the method for the treatment of ED according to the present invention may be targeted to at least one or more of the penis vasculature for example including but not limited to cavernosal artery, dorsal artery, bulbar artery, cavernosal vein, dorsal vein and bulbar vein, any combination thereof or the like.

Optionally the method for the treatment of ED according to the present invention may target at least one phase of the erectile cycle for example including but not limited to initiation, generation, maintenance, and detumescence, any combination thereof or the like.

Optionally the method for the treatment of ED according to the present invention may be targeted toward at least one erectile function for example including but not limited to arterial inflow, sufficient corpora cavernosal expansion, competent venous sinusoidal outflow occlusion, or any combination thereof.

Optionally the method for the treatment of ED according to the present invention targets at least one or more penile anatomy, for example including but not limited to corpora cavernosa, corpus spongiosum, and glans, ischiocavernous muscle, or any combination thereof or the like portion of the penile anatomy.

An optional embodiment according to the present invention provide for a shockwave treatment apparatus for the treatment of erectile dysfunction comprising: shockwave applicator comprising a shockwave generator adept for generating shockwaves having a focal treatment zone comprising most of the corpus cavernosum of the penis; wherein the focal treatment zone comprises dimensions of length and width wherein the focal zone length comprises most of the length of the penis and the width comprises most of the width of the penis; and a penis treatment coupling assembly comprising a proximal opening for accepting and retaining the penis for undergoing shockwave treatment according to the present invention.

Optionally and preferably the penis treatment coupling assembly further comprises a distal opening for accepting a shockwave treatment applicator.

Optionally and preferably the penis treatment coupling assembly further comprises a penis treatment neck for retaining and accepting a penis. Most preferably the treatment neck extends from the proximal opening. Optionally the treatment neck may be aligned with the shockwave generator. Optionally, the treatment neck may further comprise a distal opening.

Optionally the penis treatment coupling assembly may be provided in the form of a flexible ESWT cushion treatment head therein comprising a penis positioning treatment neck and a proximal opening for accepting and retaining a penis within the positioning treatment neck. Optionally and preferably the flexible ESWT cushion treatment head and the shockwave applicator are securely coupled preferably forming a continuous lumen containing an aqueous solution for propagating generated shockwaves.

Optionally, the shockwave treatment apparatus according to the present invention may further comprise at least one vacuum inlet and outlet. Optionally the vacuum inlet and outlet may for example be provided separately or in a single double lumen tube. Optionally the vacuum inlet and outlet may provide for positioning a penis into a penis positioning treatment neck. Optionally, the vacuum inlet and outlet may provide a vacuum strength of about 0.1 atm to 0.8 atm, most preferably the vacuum may be applied within the penis positioning treatment neck.

Most preferably, the proximal opening of the penis treatment coupling assembly further comprises a seal for maintain an aqueous environment about the treated penis. Most preferably, the seal further facilitates the formation of a contiguous aqueous environment to allow for the transmission and propagation of shockwaves from about the shockwave treatment applicator generator to about the root of the penis.

Optionally the penis treatment coupling assembly housing may be provided in a plurality of optional forms for example including but not limited to disposable single time use, multiuse, customized for an individual user, elastic membrane or the like.

Optionally the shockwave applicator may be provided as commercial off the shelf (COTS) shockwave applicator and or generator.

Optionally, the apparatus according to the present invention produces a shock wave regimen determined based on at least one or more parameters for example including but not limited to shockwave parameters, treatment protocol parameters, anatomical parameters, or the like. Optionally, shockwave parameters may for example include but are not limited to number of shockwaves, frequency of shockwaves and intensity of the shockwave, or the like.

An optional embodiment of the present invention provides a shockwave treatment device for the treatment of a penis experiencing erectile dysfunction comprising:

An upper housing comprising a shockwave generator adept for generating a shock wave having a focal zone comprising most of the penis; and a lower housing comprising a treatment neck and a proximal opening for accepting and retaining the penis within the a treatment neck;

a lumen spanning the lower housing and the upper housing filled with an aqueous solution for propagating the generated shockwave; and at least one vacuum inlet and outlet for drawing the penis into the treatment neck.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4 is a schematic Gantt chart of an ESWT treatment protocol according to an optional embodiment of the present invention.

FIG. 5B provides a schematic depiction of the preferred focal zone according to an optional embodiment of the present invention.

DESCRIPTION OF THE PREFERRED EMBODIMENTS

The principles and operation of the present invention may be better understood with reference to the drawings and the accompanying description.

Figure 1A:
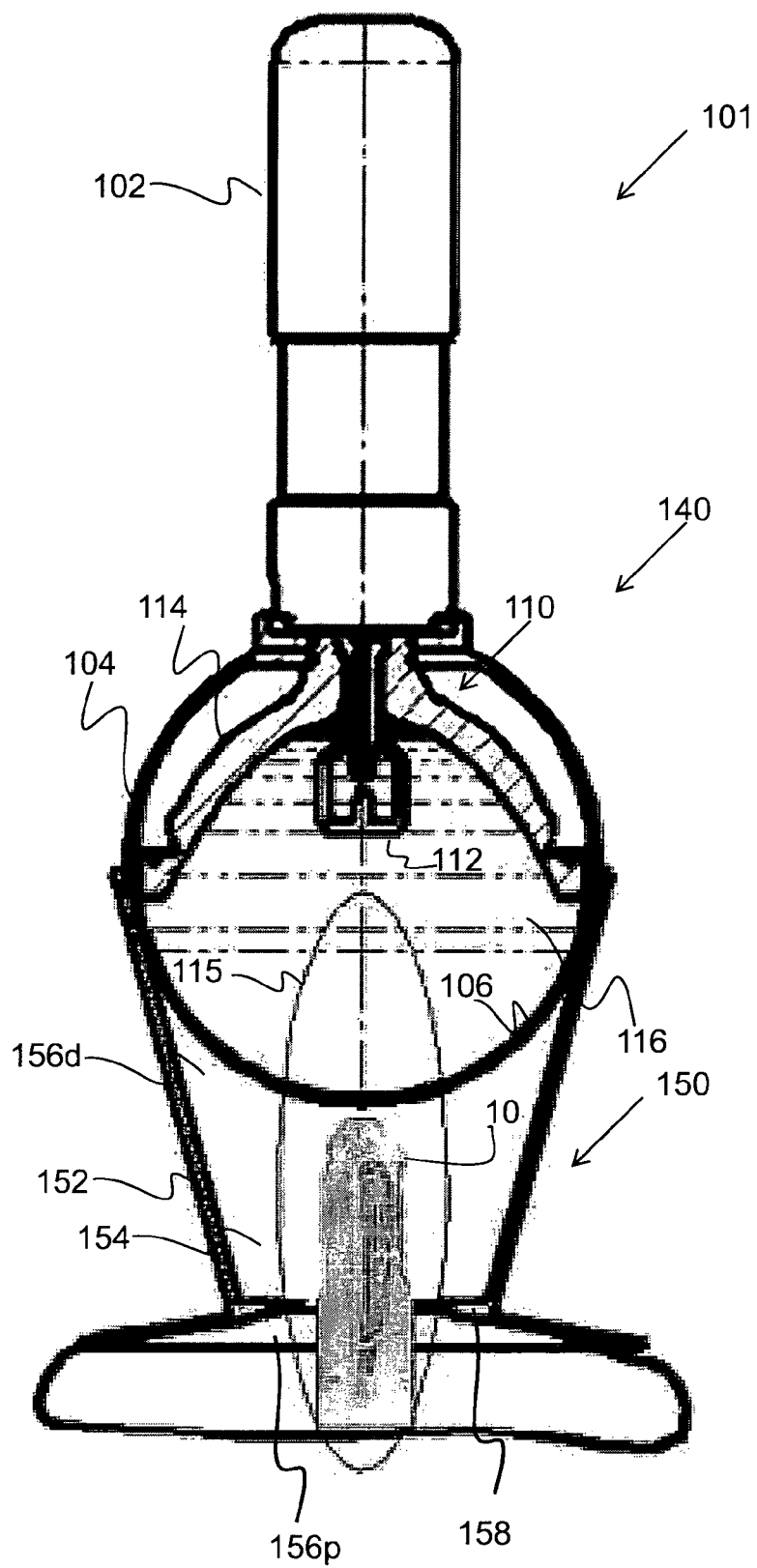
FIGS. 1A-B are schematic illustrative diagrams of optional device configurations according to an optional embodiment of the present invention.

The following figure reference labels are used throughout the description to refer to similarly functioning parts.
1-7 optional treatment zones along the penis;
10 penis;
100 ESWT applicator;
101 ESWT apparatus;
102 handle;
104 shockwave applicator housing;
106 flexible ESWT cushion treatment head;
108 seal;
110 shock wave generator ensemble;
112 spark plug;
114 shockwave reflector;
115 ESWT focal treatment zone and/or therapeutic area;
116 shockwave transmission and/or propagation aqueous medium filled lumen;
120 penis positioning treatment neck;
122 proximal opening to penis positioning treatment neck;
126 connector;
130 pressure/vacuum inlet and outlet;
140 shockwave treatment applicator;
150 penis treatment coupling assembly;
152 penis treatment assembly housing;
154 shockwave coupling and transmission and/or propagation lumen;
156d distal opening to penis treatment assembly;
156p proximal opening to penis treatment assembly;
158 penis treatment assembly seal;
160 penis treatment neck;
162d distal opening;
162p proximal opening;
164 shockwave coupling and transmission/propagation lumen;

FIG. 1A provides a schematic illustration of an optional embodiment of ESWT apparatus 101 according to the present invention. Apparatus 101 comprises a shockwave treatment applicator 140 and penis treatment coupling assembly 150. Optionally and preferably shockwave treatment device 140 is a commercial off the shelf (COTS) ESWT generator as is known in the art. Treatment applicator 140 is optionally provided as electrohydraulic, electromagnetic, piezoelectric or the like shockwave generator as is known and accepted in the art. Optionally and preferably treatment applicator 140 is provided as a spark gap generator.

Most preferably penis treatment coupling assembly 150 is provided as an attachment element that may be coupled to shockwave treatment applicator 140. Optionally and preferably penis treatment coupling assembly 150 is a single use disposable applicator. Optionally penis treatment coupling assembly 150 may be provided as a multiuse personalized treatment applicator.

Treatment coupling assembly 150 preferably comprises a penis treatment housing 152 comprising at least two openings 156: a first, proximal, opening 156p and a second, distal, opening 156d. Optionally penis treatment housing 152 may be provided in optional shapes preferably amenable to accept the treated portion of the body, most preferably penis 10, and to be associated and/or coupled with treatment applicator 140. Optionally housing 152 may be provided in the form of a cone, cylinder or the like shape. Optionally housing 152 may be provided in customized form.

Most preferably proximal opening 156*p* is provided to accept penis 10. Optionally proximal opening 156*p* is provided with a seal 158.

Most preferably distal opening 156*d* is provided for associating and/or coupling penis treatment coupling assembly 150 with shockwave therapy device 140. Optionally and preferably shockwave therapy applicator 140 is placed over opening 156*d* and helped into place by a user. Optionally distal opening 156*d* may be coupled with shockwave therapy applicator 140, for example with threading on the inner surface housing 152 over opening 156*d* corresponding to threading on the external applicator 140. Optionally distal opening 156*d* may be associated with flexible ESWT cushion treatment head 106 with suction, pressure, or the like means for coupling. Optionally distal opening 156*d* may be associated with treatment head 106 with connectors for example alligator clips, snaps, hook and loop or the like as is known in the art.

Most preferably housing 152 forms a shockwave propagation lumen 154 that is most preferably provided with an aqueous solution for example including but not limited to water, treated water, ionized water, gel, medicated solution, oil, or the like solution. Most preferably seal 158 is provided to maintain an aqueous solution within shockwave propagation lumen 154. Most preferably shockwave treatment applicator 140 generates a shockwave, for example with spark plug 112 and reflector 114 that propagates through an aqueous shockwave propagation medium filled lumen 116 and through to shockwave propagation lumen 154 most preferably providing a treatment focal zone 115 comprising penis 10 and most preferably at least a portion of the corpus cavernosa. Optionally a focal zone may be directed to at least one and up to about seven areas 1-7 (FIG. 5A) along the penis, optionally and preferably two treatment zones 1-7 along the penis and most preferably one treatment zone 115 along the penis. Most preferably focal zone 115 comprises the full length of penis 10, providing for a single ED treatment zone. Focal zone 115 optionally comprises at least a portion of the corpus cavernosa, for example at least about 50%, more preferably at least about 70%, more preferably at least about 80%, more preferably at least about 90%, most preferably about 100%.

Figure 1B:
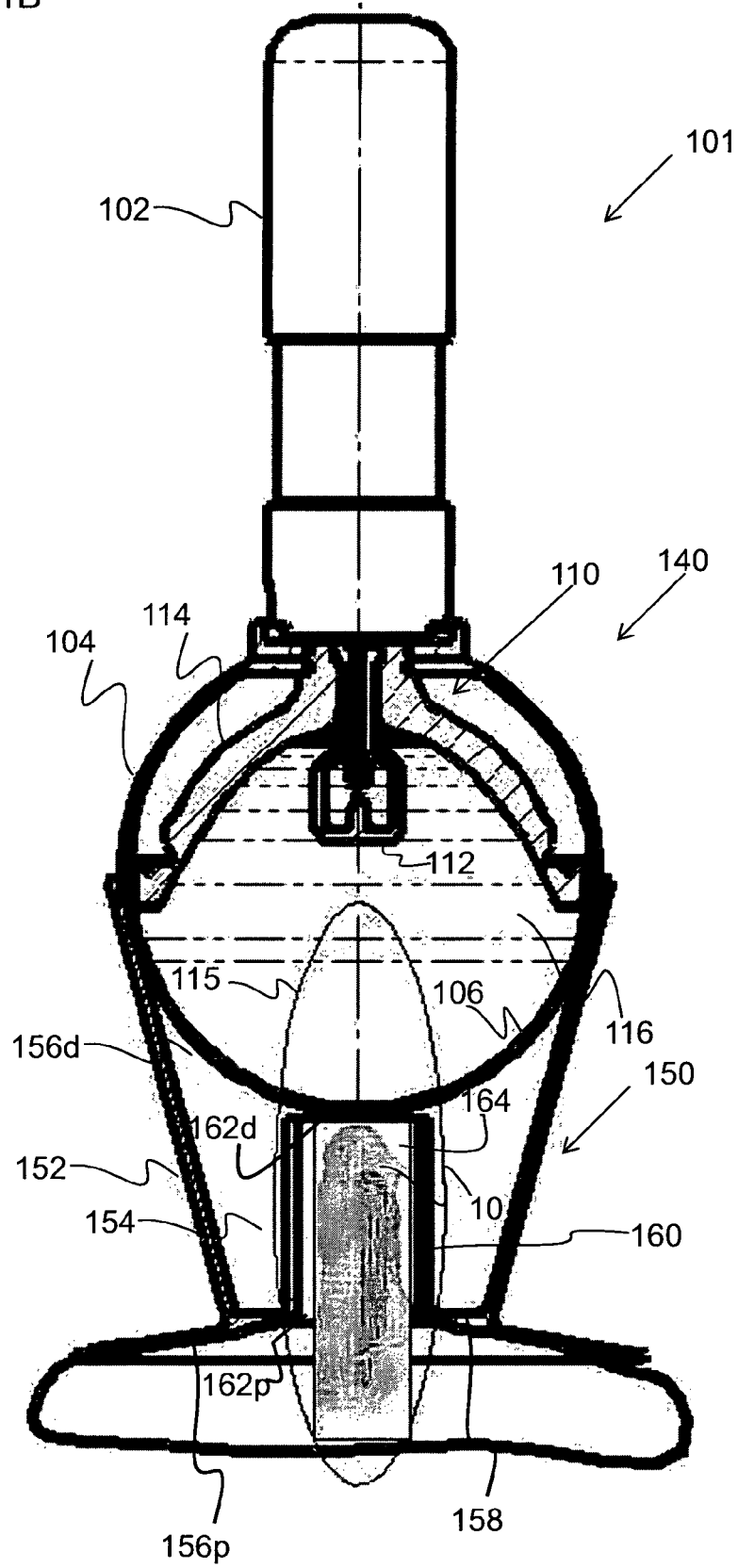

FIG. 1B provides an optional embodiment of the penis treatment coupling assembly 150 described FIG. 1A. Penis treatment coupling assembly 150 further comprises a penis treatment neck 160 for accepting and retaining penis 10 during shockwave treatment with ESWT applicator 140. Optionally penis treatment neck 160 comprises a distal opening 162*d* and proximal opening 162*p*. Optionally and preferably the proximal end of penis treatment neck 160 comprises seal 158 about proximal opening 162*p* for sealing and maintaining an aqueous environment within treatment neck lumen 164. Most preferably treatment neck 160 comprises an aqueous environment within lumen 164.

Optionally treatment neck 160 may further comprise at least one or more opening along its posterior and/or anterior sides. Optionally such anterior and/or posterior opening provides for localized targeted treatment area with focal zone 115.

Most preferably shockwave treatment device 140 generates a shockwave that propagates through shockwave propagation lumen 154 as described above and treatment neck 160 preferably in an aqueous solution adapted to form treatment focal zone 115 comprising penis 10 and most preferably the corpus cavernosa.

Figure 2:
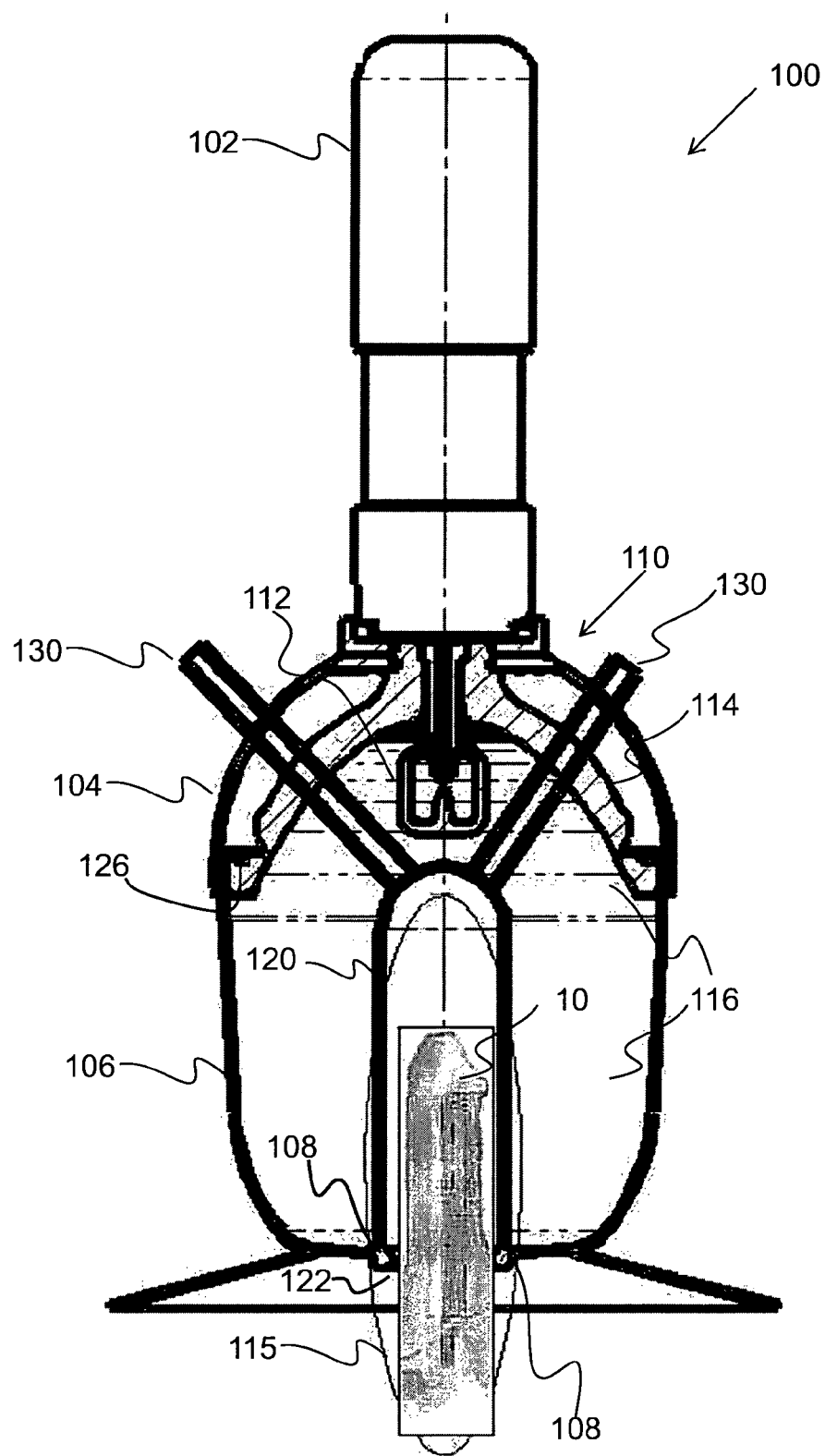
FIG. 2 is a schematic illustrative diagram of an exemplary device according to an optional embodiment of the present invention.

FIG. 2 shows a schematic illustrative diagram of an exemplary ESWT applicator 100 according to an optional embodiment of the present invention for the delivery ESWT for the treatment of ED. ESWT applicator 100 preferably comprises a handle 102, shockwave applicator housing 104 and treatment head 106. Most preferably shockwave applicator housing 104 comprises shockwave generator apparatus 110 for generating and propagating shockwave treatment. Shockwave generator apparatus 110 may be provided as electrohydraulic (also referred to as spark gap), electromagnetic (also referred to as EMSEA), or piezoelectric generators as is known and accepted in the art. Optionally shockwave generator apparatus 110 is provides in the form of a spark gap comprising spark plug 112 shockwave reflector 114 that are preferably immersed in an transmission and/or propagation medium 116 most preferably an aqueous solution confined by treatment head 106. Most preferably medium 116 comprises an aqueous environment for transmitting/propagating the generated shockwave, optionally water, treated water, gel, ionized water, oil or the like aqueous solution as is know in the art.

Most preferably treatment head 106 is coupled to shockwave applicator housing 104 and shockwave generator ensemble 110 via connectors 126. Optionally and preferably connectors 126 are provided in the form of hermetic seal. Treatment head 106 forms a shockwave propagation lumen 116 wherein most preferably a shockwave generated by shockwave generator 110 is propagated through aqueous environment 116 optionally in the form of water, treated water, gel, ionized water, oil or the like aqueous solution as is know in the art. Most preferably shockwave generator 110 provides a shockwave that propagates through the aqueous solution to form treatment focal zone 115 comprising penis 10 and most preferably the corpus cavernosa.

Most preferably lumen 116 is provided with a penis positioning treatment neck 120 comprising a proximal opening 122 provided to accept a penis 10 into treatment neck 120 where optionally and preferably most of the ESWT for ED is provided.

Most preferably shockwaves according to a treatment protocol according to an optional embodiment of the present invention for ED is generated by shockwave generator 110 propagating through lumen 116 comprising aqueous solution and onto treatment neck 120. Most preferably treatment neck 120 is filled with an aqueous solution for example including but not limited to water, oil, treated water, gel, ionized water or the like aqueous solution as is know in the art. Preferably aqueous solution is maintained within treatment neck 120 with seal 108. Most preferably the aqueous solution within treatment neck 120 provides a medium to propagate shockwaves onto penis 10.

Optionally and preferably shockwave applicator 100 further comprises vacuum inlet and outlet 130 associated with and/or connected to treatment neck 120. Most preferably vacuum inlet and outlet 130 provides for vacuum within treatment neck 120, providing vacuum of about 0.3-0.4 atm. Optionally seal 108 provided at the base of treatment neck 120 maintains vacuum within treatment neck 120, providing for drawing penis 10 into treatment neck 120.

Figure 3:
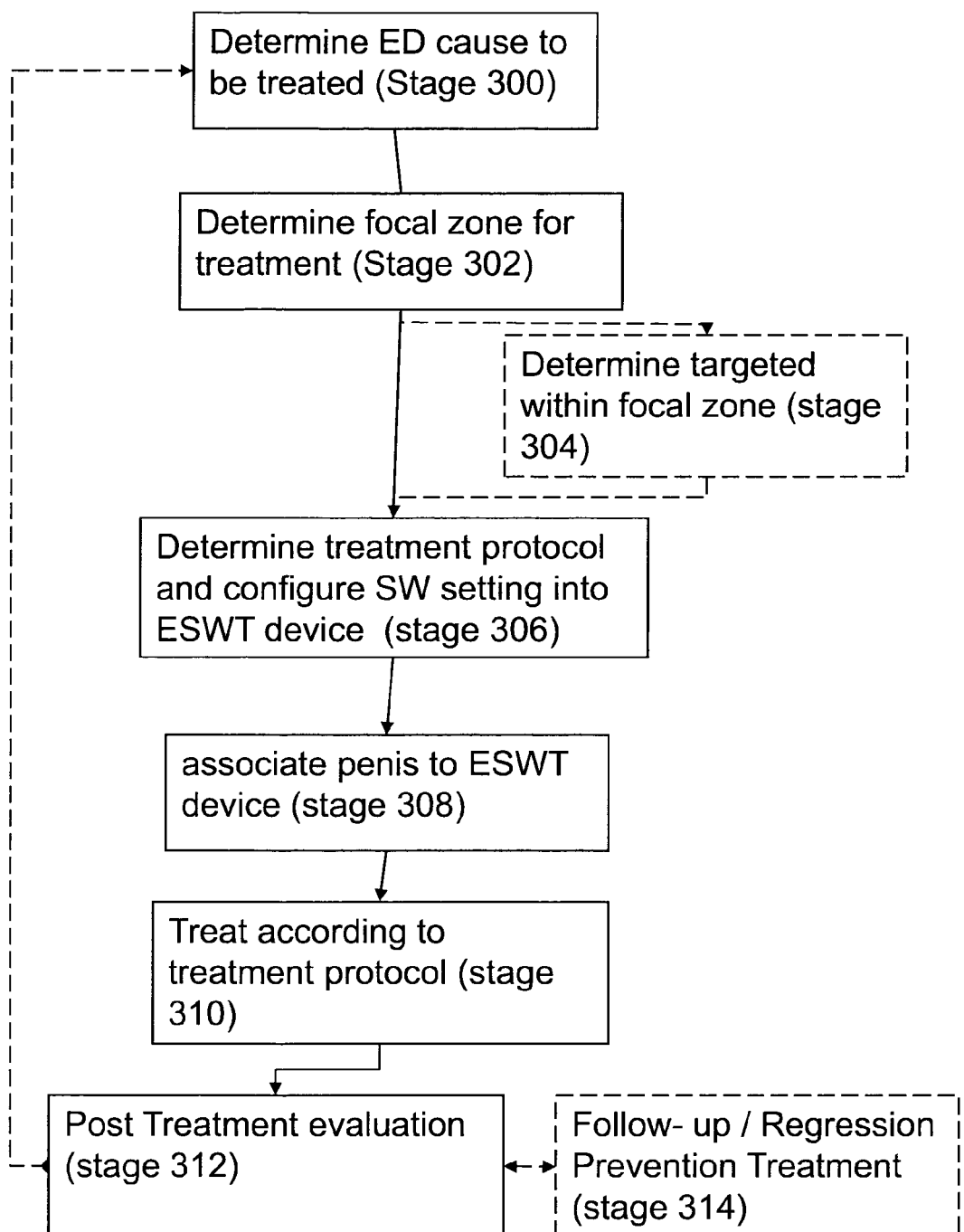
FIG. 3 is a flowchart of an exemplary method according to the present invention for ESWT for ED.

FIG. 3 shows a flowchart of an optional method of treatment of ED according to an optional embodiment of the present invention. First in stage 300 at least one suspect cause of ED is determined along with at least one treatment protocol for treating it. Next in stage 302, the ESWT treatment focal zone, for example 115 of FIGS. 1-2, 5A-B is determined most preferably for improving treatment results. Optionally, a localized and/or primary ESWT targeted zone with the focal zone, for example 115 of FIGS. 1-2, 5A-B, is determined in stage 304. Most preferably focal zone 115 comprises the full length of penis 10, providing for a single ED treatment zone. Focal zone 115 optionally comprises at least a portion of the corpus cavernosa, for example at least about 50%, more preferably at least about 70%, more preferably at least about 80%, more preferably at least about 90%, most preferably about 100%. Next in stage 306, an appropriate treatment protocol is determined and ESWT device and applicator, for example applicator 140 of FIGS. 1A-B, is configured to provide the treatment. Next in stage 308, the ESWT device according to any of the optional embodiments of the present invention is associated with a penis experiencing ED, as shown in FIGS. 1 and 2, and thereafter treatment is provided in stage 310 as determined in stage 306.

Next in stage 312, treatment, assessment and evaluation is provided for determining follow up treatment to undertake, optionally to provide further treatment with a focal treatment zone, as described in stage 300, or to continue with follow up treatments in stage 314.

Optionally stage 314 is provided for follow up treatments as an addition to the treatment protocol defined in 306. Optionally stage 314 may be used to provide for continued treatment, complimentary treatment, ongoing preventative treatment, regression prevention treatment, treatment for episodes of ED or the like treatment in continuation of the treatment protocol of stage 306. Optionally following stage 314 treatment is reevaluated in stage 312.

Optionally treatment protocol determined in stage 306 comprises at least one or more parameters, for example including shockwave parameters, treatment protocol parameters, anatomical parameters or the like parameters. For example protocol parameters may include but are not limited to the number of treatment sessions, treatment protocol duration, period of active/inactive treatment sessions, duration of interval periods without ESWT, number of treatment zones on the treated penis, number of shockwaves per zone, total number of shockwaves, treatment intensity, treatment frequency, or the like parameters. Table 1 below summaries the optional treatment parameters and their optional value ranges for treating ED with the ESWT device according to the present invention.

TABLE 1

| S.N. | Parameter Group | Parameter | Value Range |
| --- | --- | --- | --- |
| 1 | Protocol parameters | Number of treatment sessions | 12 (3-18) |
| 2 | | Treatment Protocol Duration | 3-18 weeks |
| 3 | | Weeks of active Treatment sessions | Weeks 1, 2, 3, and 7, 8, 9, - twice a week |
| 4 | | Weeks of non-treatment Interval | Weeks 4, 5, 6, - treatment recess |
| 5 | Anatomical parameters | Number of treatment zones on the treated penis | 1-7 |
| 6 | Shockwave Parameters | Number of Shockwaves per zone | 300 (100-500) |
| 7 | | Total number of shockwaves per session | 300-3500 |
| 8 | | Shockwave | 50-200 bar = 0.09 mJ/mm² |

TABLE 1-continued

| S.N. | Parameter Group | Parameter | Value Range |
| --- | --- | --- | --- |
| 9 | | intensity Shockwave Frequency | (0.02-0.18) 120/min (60-240) |

Optionally the number of treatment sessions for ED treatment protocols may comprise from about 3 to about 18 active treatment session, optionally about 12 treatment session.

Optionally the duration of one treatment protocol for ED treatment may comprise from about 3 weeks to about 18 weeks. Optionally and preferably the protocol duration comprises periods of active ESWT treatment and period of inactive and/or rest periods without ESWT treatment. Optionally during weeks of active treatment session treatment may optionally be delivered at least once a week and more preferably at least twice a week, as shown in the schematic Gantt chart of FIG. 4.

Figure 5A:
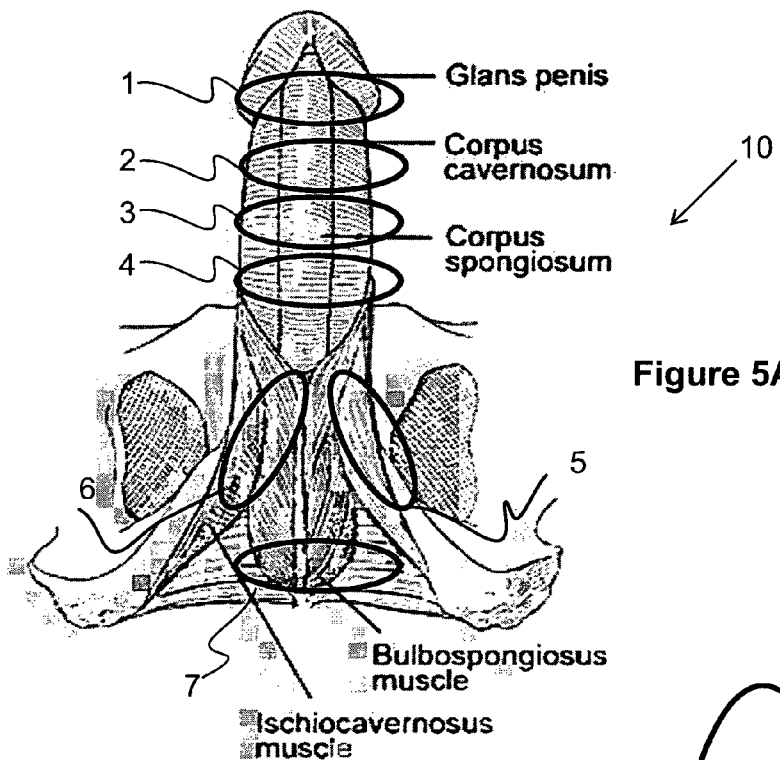
FIGS. 5A-B are schematic diagrams of optional treatment zones for Erectile Dysfunction.
Figure 5B:
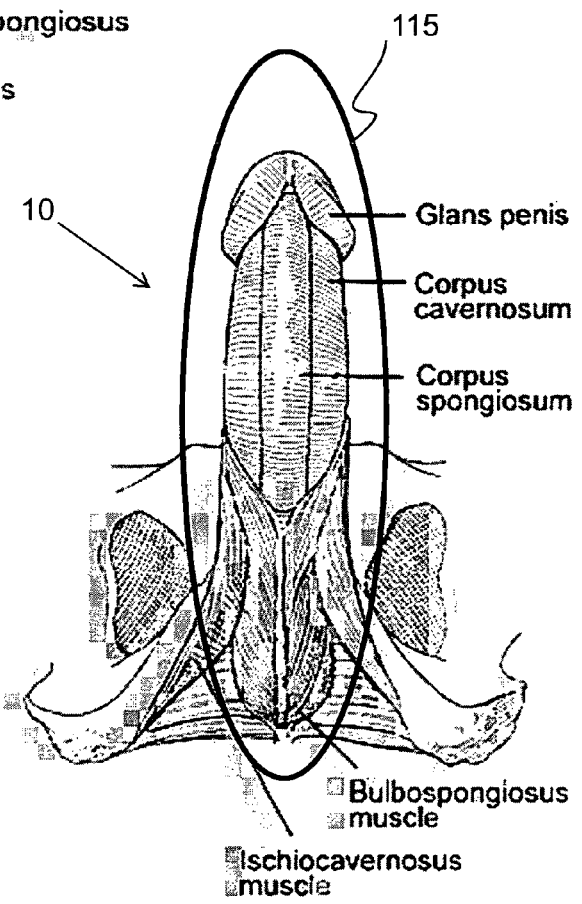

Optional anatomical parameters are depicted in FIGS. 5A-B providing a schematic illustration of optionally treatment zones that may be utilized in the treatment protocol according to the present invention most preferably provided with the device according the present invention. FIG. 5A shows optional localized treatment zones 1-7 distributed along a penis 10 while FIG. 5B shows a central treatment zone 115, incorporating most of the length of penis 10. FIG. 5B provides a further depiction of the most preferred focal treatment zone according to the present invention as previously described in FIGS. 1-2.

Optionally the ESWT apparatus, for example 100 and/or 101, according to the present invention previously described in FIGS. 1-2 may produce at least one of the optional focal treatment zones, shown in FIGS. 5A and 5B, for example including but not limited to treatment zones 1-7 and/or 115. Optionally and preferably the ESWT apparatus 100 and/or 101 may provide for a plurality of treatment zones for example including but not limited to zones 1-7 and/or 115. Preferably the focal treatment zone may comprise of at least two treatment zones for example including but not limited to zones 1-7. Most preferably, ESWT apparatus 100 and/or 101 provide for focal treatment zone 115 comprising most of penis 10.

Optionally focal treatment zones 1-7, 115 used with ESWT apparatus 100 and/or 101 may vary according to the symptoms and/or causes of the ED being treated, for example including but not limited to at least one or more of physiologic, neurogenic, vasculogenic, hormonal, or psychologic factors or the like.

Optionally and preferably a combination of any of focal treatment zones 1-7 may be utilized. Most preferably focal zone 115 of the ESWT device according to any of the optional embodiments previously described and illustrated in FIGS. 1-2, may be further fine tuned to treat a particular zone along the treated penis. Optionally the targeted treatment zone, for example 115 of FIGS. 1-2, 5B, may for example include but is not limited at least one or more of corpora cavernosa, corpus spongiosum, root of the penis, bulbos and glans.

Optionally targeted treatment zone 115 provides a single treatment zone spanning the length of the treated penis for example including from about 50% of the penis to about 100% of the penis.

Optionally the shockwave parameters for example comprise parameters including but not limited to shockwave frequency, shockwave intensity and number of shockwaves delivered. Optionally and preferably the shockwave parameters are controllable and may be set in accordance with a particular treatment protocol, for example in stage 306 of FIG. 3 and schematically shown in FIG. 4 as described above. Optionally, shockwave parameters may be determined and defined based on the anatomical area being treated, as shown and described above in FIGS. 5A and 5B. Optionally shockwave parameters may be determined and defined according to at least one or more effective treatment sought for example including but not limited to vasodilatation, vasoconstriction, angiogenesis, endothelial function, neuronal, neural regeneration, decalcification, increase cytoplasmic calcium concentration, reduce cytoplasmic calcium concentration, inhibition of PDE5, enzymatic inhibition, enzymatic excitation, or the like taken alone or in any combination thereof.

Optionally the total number of shockwaves provided during a single active treatment session comprises up to about 5000 shockwaves, more preferably from about 300 to about 3500 shockwaves. Optionally and preferably the total number of shockwave may be determined by the number of targeted treatment zones, for example zones 1-7, 115 as shown in FIGS. 5A-B. Optionally when a plurality of zones are treated each targeted treatment zone is provided with up to about 700 shockwaves, more preferably from about 100 to about 500 shockwaves and most preferably up to about 300 shockwaves per targeted treatment zone. Most preferably the device and apparatus of the present invention provides for a single treatment zone, for example 115 of FIGS. 1, 2, 5B spanning the length of the treated penis optionally and preferably reducing the overall number of shockwaves needed for comprehensive treatment.

Optionally shockwave intensity provided during a single active treatment according to the present invention comprises shockwaves intensity of up to about 300 bar, more preferably from about 50 bar up to about 200 bar, more preferably about 100 bar, most preferably about 125 bar. Optionally the shockwave intensity provided during a single active treatment comprises shockwaves intensity of up to about 0.25 mJ/mm$^2$, more preferably from about 0.02 mJ/mm$^2$ up to about 0.18 mJ/mm$^2$, and most preferably at about 0.09 mJ/mm$^2$. Optionally shockwave intensity parameters measurement may for example be provided in the unit measurements of bar and/or mJ/mm$^2$ or the like equivalent unit measurement for shockwave intensity as is known and accepted in the art.

Optionally shockwave frequency provided during a single active treatment according to the present invention comprises shockwaves frequency of up to about 300 shockwaves per minute, optionally from about 60 up to about 240 shockwaves per minute and optionally and preferably about 120 shockwaves per minute.

While the invention has been described with respect to a limited number of embodiments, it will be appreciated that many variations, modifications and other applications of the invention may be made.

What is claimed is:

1. A method for the treatment of Erectile Dysfunction, the method comprising:
    (a) associating a penis with a shockwave generating device within an aqueous environment using a penis treatment coupling assembly comprising: a proximal opening and a treatment neck for accepting and retaining the penis for undergoing a shockwave treatment; wherein the treatment neck extends from the proximal opening; and wherein the treatment neck is aligned with the shockwave generating device; and
    (b) applying a shockwave regimen to the penis wherein the shockwave generating device produces shockwaves that are directed at a focal zone comprising at least a portion of corpus cavernosa of the penis; the shockwave generating device utilizing an electrohydraulic or an electromagnetic shockwave generating mechanism.

2. The method of claim 1 wherein the shockwaves are directed at a focal zone which includes most of the corpus cavernosa.

3. The method of claim 1 wherein the shockwaves are directed at a focal zone which comprises most of the length of the penis.

4. The method of claim 1 wherein the shockwave regimen promotes at least one or more therapies for treating symptoms of Erectile Dysfunction chosen from the group consisting of: vasodilatation, vasoconstriction, angiogenesis, endothelial function, neuronal, neural regeneration, decalcification, increase cytoplasmic calcium concentration, reduce cytoplasmic calcium concentration, inhibition of PDE5, enzymatic inhibition, enzymatic excitation, or any combination thereof.

5. The method of claim 1 wherein the shock wave regimen is determined based on at least one parameter chosen from the group consisting of shockwave parameters, treatment protocol parameters, and anatomical parameters.

6. The method of claim 5 wherein the shockwave parameters comprise number of shockwaves, frequency of shockwaves and intensity of the shockwave.

7. The method of claim 6 wherein the parameters are selected from at least one of: shockwave intensity in a range between 50 bar to 200 bar; shockwave frequency in a range between 60 to 300 shockwaves per min; and the number of shockwaves is below 3500 per session.

8. The method of claim 5 wherein the anatomical parameters comprise a selection of one or more treatment zones selected from at least seven treatment zones within the penis and corpus cavernosa.

9. The method of claim 5 wherein the anatomical parameters comprise a single focal zone including up to about 90% of the corpus cavernosa of the penis.

10. The method of claim 1 further comprising placing at least a portion of the corpus cavernosa of the penis in reduced pressure environment of about 0.1 to 0.8 atm.

11. The method of claim 10 wherein the reduced pressure environment is an aqueous environment provided for by a liquid chosen from the group consisting of water, oil, and gel.

12. The method of claim 11 further comprising administering the shock wave regimen in combination with a drug or medicament.

13. The method of claim 12 wherein the medicament or drug is chosen from a group consisting of stem cells, growth factors, hormones, peptides, biologics, DNA, RNA, animal extract, plant extract, oil, gel, balm, cream, angiogenic drugs, PDE5 and vasodilating drugs.

14. The method of claim 11 wherein at least one of the shockwaves targets at least one or more of the penis vasculature chosen from the group consisting of: cavernosal artery, dorsal artery, bulbar artery, cavernosal vein, dorsal vein and bulbar vein.

15. The method of claim 11 wherein the shockwave treatment is applied at least during one phase of an erectile cycle chosen from the group consisting of initiation, generation, maintenance, and detumescence.

16. The method of claim 11 wherein at least one of the shockwaves is directed towards at least one or more penile anatomy chosen from the group consisting of corpora cavernosa, corpus spongiosum, and glans.

17. A shockwave treatment apparatus for the treatment of erectile dysfunction comprising:
   (a) shockwave applicator comprising a shockwave generator adept for generating shockwaves utilizing an electrohydraulic or electromagnetic shockwave generating mechanism, the shockwave generator produces the shockwaves that are directed to a focal treatment zone comprising at least a portion of a corpus cavernosum of a penis; wherein the focal treatment zone comprises dimensions of length and width, wherein the length of the focal treatment zone comprises most of the length of the penis and the width of the focal treatment zone comprises most of the width of the penis; and
   (b) a penis treatment coupling assembly comprising a proximal opening and a treatment neck for accepting and retaining the penis for undergoing a shockwave treatment; wherein the treatment neck extends from the proximal opening; and wherein the treatment neck is aligned with the shockwave generator and wherein the treatment neck is configured to provide an aqueous environment along a length of the treatment neck.

18. The shockwave treatment apparatus of claim 17 wherein the penis treatment coupling assembly further comprises a distal opening for accepting the shockwave applicator.

19. The shockwave treatment apparatus of claim 17 wherein the penis treatment coupling assembly is provided in the form of a flexible extracorporeal shockwave therapy ('ESWT') cushion treatment head.

20. The shockwave treatment apparatus of claim 18 wherein the penis treatment coupling assembly is provided in the form of a flexible extracorporeal shockwave therapy ('ESWT') cushion treatment head that is coupled with the shockwave applicator, forming a continuous lumen containing an aqueous solution for propagating the generated shockwaves.

21. The shockwave treatment apparatus of claim 20 further comprising at least one vacuum inlet and outlet wherein the vacuum inlet and outlet provides for positioning the penis in a penis positioning treatment neck; and wherein the vacuum inlet and outlet provide a vacuum strength of about 0.1 to 0.8 atm within the penis positioning treatment neck.

22. The shockwave treatment apparatus of claim 17 wherein the proximal opening comprises a seal for maintaining the aqueous environment.

23. The shockwave treatment apparatus of claim 22 wherein the seal provides for maintaining a contiguous aqueous environment along the length of the penis from about the glans to the bulbos.

24. The shockwave treatment apparatus of claim 17 wherein the penis treatment coupling assembly is disposable.

25. The shockwave treatment apparatus of claim 17 wherein the penis treatment coupling assembly is customized for multiuse.

26. The shockwave treatment apparatus of claim 17 wherein the shockwave applicator produces a shockwave based on at least one parameter chosen from the group consisting of shockwave parameters, number of shockwaves, frequency of shockwaves, intensity of shockwave, treatment protocol parameters, and anatomical parameters.

* * * * *